United States Patent [19]  [11]  4,204,065
Bodor  [45]  May 20, 1980

[54] SOFT QUATERNARY SURFACE ACTIVE AGENTS AND METHOD OF USING SAME

[75] Inventor: Nicolae S. Bodor, Lawrence, Kans.

[73] Assignee: Interx Research Corporation, Lawrence, Kans.

[21] Appl. No.: 969,255

[22] Filed: Dec. 13, 1978

Related U.S. Application Data

[63] Continuation of Ser. No. 726,841, Sep. 27, 1976, abandoned, which is a continuation-in-part of Ser. No. 615,519, Sep. 22, 1975, Pat. No. 3,989,711.

[51] Int. Cl.² .......................................... A61K 31/465
[52] U.S. Cl. ........................ 546/316; 548/134; 548/214; 548/247; 548/341; 260/239 E; 260/326.1; 260/326.13 D; 424/244; 424/250; 424/251; 424/258; 424/263; 424/266; 424/770; 424/774; 544/39; 544/224; 544/237; 544/283; 544/335; 544/336; 544/347; 544/353; 546/146; 546/174; 546/318; 546/334; 546/341; 546/342; 548/378
[58] Field of Search .......... 546/316, 318, 341, 334–342

Primary Examiner—Glennon H. Hollran
Assistant Examiner—Lisa Jones
Attorney, Agent, or Firm—Burns, Doane, Swecker & Mathis

[57] ABSTRACT

Soft quaternary surface active agents having the formula:

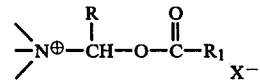

(I)

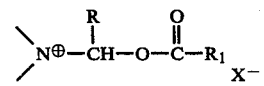

(II)

wherein >N represents a tertiary open chain or cyclic aliphatic amine; wherein >N represents an unsaturated amine; wherein R represents a member selected from the group consisting of a hydrogen atom, a $C_1$–$C_{20}$ open chain or cyclo alkyl group, a $C_1$–$C_{20}$ alkoxyalkyl group, a $C_1$–$C_{20}$ acyloxyalkyl group, a $C_1$–$C_{20}$ haloalkyl group, a $C_1$–$C_{20}$ carboxyalkyl group, an aryl group, and a substituted aryl group, whose substituents are selected from the group consisting of a halogen atom, an O—$C_1$–$C_4$ alkyl group, an O—$C_1$–$C_8$ acyl group, a nitro group, a carboxyl group, and a carboethoxy group; wherein $R_1$ represents a $C_9$–$C_{22}$ straight or branched alkyl group, a —$(CH_2)_n$—

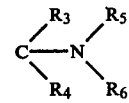

group, wherein $R_3$, $R_4$, $R_5$ and $R_6$ are each selected from the group consisting of a hydrogen atom, a methyl group or an ethyl group, a $C_0$–$C_{22}$ straight or branched alkyl-$(CH_2)_n$

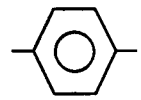

$(CH_2)_m CH_3$ group, wherein n in each occurrence and m represents an integer of from 0 to 22, an A-$CH_2$

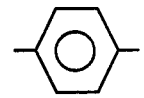

$CH_2$-A-$CH_3$ group, wherein A represents a $C_0$–$C_{22}$ straight or branched alkyl group as above or a —$(CH_2CH_2O)$ group, wherein the p represents an integer of from 0 to 22, and the residue of any naturally occurring bile acid or synthetic derivative thereof; and wherein X represents a halogen atom or any other organic or inorganic monovalent anion are disclosed.

All compounds encompassed within the above-described generic formulae find use as "soft" antibacterial agents of extremely low toxicity.

108 Claims, No Drawings

SOFT QUATERNARY SURFACE ACTIVE AGENTS AND METHOD OF USING SAME

CROSS REFERENCE TO RELATED APPLICATIONS

This is a continuation of application Ser. No. 726,841, filed Sept. 27, 1976 now abandoned, which in turn is a continuation-in-part of Ser. No. 615,519, filed Sept. 22, 1975, now U.S. Pat. No. 3,989,711.

BACKGROUND OF THE INVENTION

1. Field of the Invention

The present invention is directed to soft quaternary surface active agents and more specifically, to soft quaternary surface active agents characterized as being substantially antibacterial in nature but of low toxicity due to their ability to degrade into relatively nontoxic, nonquaternary by-products subsequent to exerting their antibacterial activity.

2. Description of the Prior Art

One of the basic methods of synthesis of the compounds encompassed within the above-described generic formula consists in reacting a compound of the formula (A) below wherein R and $R_1$ are defined as above with a compound of the formula (B) below, wherein R, $R_1$, $\rightarrow$N and $\gg$N and X are defined as above:

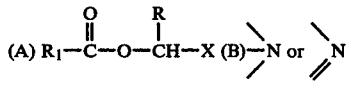

A few of the compounds of formula (A) above are old in the art and are formed by the reaction between an aldehyde (R—CHO) and an acyl halide

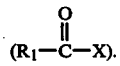

See, R. Adams and E. H. Vollweiler, *J. Amer. Chem. Soc.*, 40, 1732 (1918); H. E. French and R. Adams, ibid., 43, 651 (1921); L. H. Ulich and R. Adams, ibid., 43, 660 (1921).

Thus, preparation of the compounds of formula (A) can be described by reference to the following equation, wherein R and $R_1$ are defined as above:

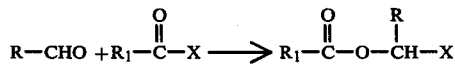

An alternate method of preparing the compounds of formula (A) resides in reacting a salt of the acid $R_1$-COOH with a nonsymmetric dihalo derivative

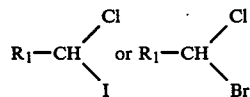

as follows:

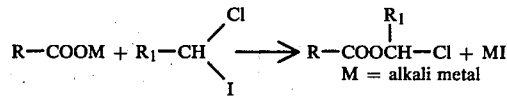

using an inert solvent such as dimethylformamide at or below room temperature.

The compounds of formula (A) have been used in the past to protect a carboxy function in the following manner:

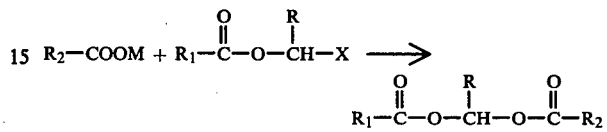

In the above equation, R and $R_1$ are defined as above; $R_2$ represents the residue of ampicillin or a salicylic acid derivative; and M represents an alkali metal salt (Na, K, etc.). See, "Acyloxymethyl Esters of Ampicillin,"W. V. Daehne, E. Fredricksen, E. Gundersen, F. Lund, P. Morch, H. J. Petersen, K. Roholt, L. Tybring, and W. V. Godfredsen, *J. Med. Chem.*, 13, 607 (1970), or British Pat. No. 1,220,457. While those compounds of formula (A) have been used as outlined above, i.e., protecting the carboxy function, this utility has no bearing on the invention disclosed and claimed herein. On the other hand, it is generally known that any activated haloalkyl compound (e.g., benzyl bromide or chloride) will react with a tertiary aliphatic amine to form the corresponding quaternary ammonium salt. However, this salt does not undergo hydrolytic cleavage, which is a necessary characteristic of the labile quaternary ammonium salts of this invention.

"Hard" quaternary salt surface active agents are known and widely used for numerous purposes in cosmetics, cleansing preparations and antimicrobial preparation, e.g., mouthwashes, shampoos, soaps, etc. These quaternary salts which are a very short chain length are highly toxic whereas those of long chain length are less toxic but only due to their inability to be readily absorbed. For instance, the $LD_{50}$ for cetylpyridinium chloride via oral versus I.P. administration is substantially greater. See Example III, infra.

In addition, it is now believed that such "hard" quaternary salt surface active agents, which alter surface tension in the liver, do, in fact, influence a number of chemical and physical processes in the liver. Consequently, such agents have an indirect toxic effect on the hepatic system.

Accordingly, a need arises for a "soft" surface active agent which, subsequent to exerting its desired effect, will "cleave" via chemical and/or enzymatic hydrolysis to release nontoxic and nonsurface active moieties. That is, it is desirable to develop a quaternary derivative which, after exerting its desired effect, will "cleave" via chemical and/or enzymatic hydrolysis to release nonquaternary, nontoxic by-products.

*U.S. Patent Application, Ser. No. 482,513—Bodor discloses similar compounds having little, if any, antibacterial activity. This application was filed on June 24, 1974 and has since been allowed.

SUMMARY OF THE INVENTION

It is one object of the present invention to provide certain quaternary surface active agents capable of exerting a substantial antibacterial effect.

It is another object of the present invention to provide quaternary surface active agents as described above which, in addition to being substantially antibacterial in nature, remain relatively nontoxic due to the ability of such agents to degrade into nontoxic by-products subsequent to exerting their antibacterial effect.

All the foregoing objects are attained with the following compounds generically described in formulas (I) and (II) below:

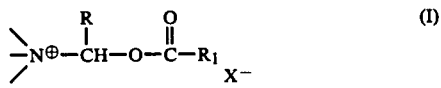

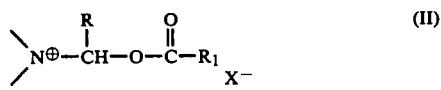

wherein→N represents a tertiary open chain or cyclic aliphatic amine; wherein→N represents an unsaturated amine; wherein R represents a member selected from the group consisting of a hydrogen atom, a $C_1$-$C_{20}$ open chain or cyclo alkyl group, a $C_1$-$C_{20}$ alkoxyalkyl group, a $C_1$-$C_{20}$ acyloxyalkyl group, a $C_1$-$C_{20}$ haloalkyl group, a $C_1$-$C_{20}$ carboxyalkyl group, an aryl group, and a substituted aryl group, whose substituents are selected from the group consisting of a halogen atom, an O—C$_1$—C$_4$ alkyl group, an O—C$_1$—C$_8$ acyl group, a nitro group, a carboxyl group, and a carboethoxy group; wherein $R_1$ represents a $C_9$-$C_{22}$ straight or branched alkyl group, a —(CH$_2$)$_n$—

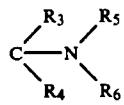

group, wherein $R_3$, $R_4$, $R_5$ and $R_6$ are each selected from the group consisting of a hydrogen atom, a methyl group or an ethyl group, a $C_0$-$C_{22}$ straight or branched alkyl—(CH$_2$)$_n$

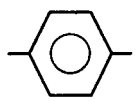

(CH$_2$)$_m$CH$_3$ group, wherein n in each occurrence and m represents an integer of from 0 to 22, an

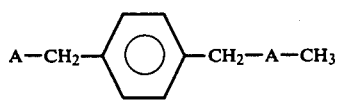

group, wherein A represents a $C_0$-$C_{22}$ straight or branched alkyl group as above or a —(CH$_2$CH$_2$O)$_p$ group, wherein the p represents an integer of from 0 to 22, and the residue of any naturally occurring bile acid or synthetic derivative thereof; and wherein X represents a halogen atom or any other organic or inorganic monovalent anion.

With regard to the above formulas (I) and (II), respectively, reference to "aryl" denotes a phenyl or naphthyl group; reference to "halo" and "halogen" in each occurrence denotes any suitable member of the halogen series, e.g., chlorine, bromine or iodine; and reference to "acyl" in the expression O-acyl denotes any convenient acyl group such as a formyl group, an acetyl group, a propionyl group, a benzoyl group, etc. It is further noted that the term "substituted" insofar as "substituted aryl" is concerned refers to the fact that the aryl function may be substituted with any one or more of those substituents specifically defined herein.

Insofar as the anion "X" is concerned, the term "organic or inorganic monovalent equivalent anion," denotes other equivalent anions such as methanesulfonate, fluorosulfonate, and tosylate.

Finally, the term "unsaturated amine" denotes N-heterocyclic unsaturated systems having 3-10 minutes in the ring, and substituted derivatives thereof where the unsaturation corresponds to the maximum number of noncumulative double bonds, provided that the nitrogen atom contains no hydrogen atom as a substituent. The following examples will sufficiently illustrate the scope of the above term:

1-Methyl-azirine 

1-Methyl-pyrrole 

1-Methyl-imidazole 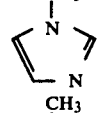

1-Methyl-pyrazole 

Pyridine 

Pyrazine 

Pyrimidine 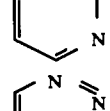

Pyridazine 

2-Methyl-isoindole 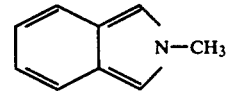

3-H-indole 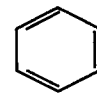

Quinoline 

Isoquinoline 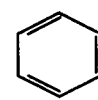

Phthalazine 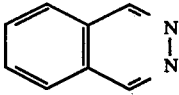

Quinoxiline 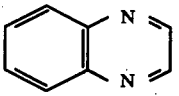

Quinazidine 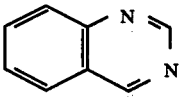

Phenazine 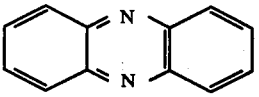

Isothiazole 

10-Methyl-phenothiazine 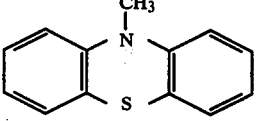

Isoxazole 

Furazan 

While the designations (≫N) and (≫N) refer to virtually any tertiary aliphatic amine and aromatic amine moiety, respectively, the following moieties are nevertheless preferred:
$C_1-C_5$ Trialkylammonium ;
Pyridine;
Methylnicotinate;
Ethylnicotinate;
Trimethylamine;
Triethylamine;
1-Benzoyloxymethyl;
N-Pivaloyloxymethyl;
Methylimidazole;
1,4-Diazabicyclo[2.2.2]octane;
Nicotinamide;
N-Ethylnicotinamide;

Finally, the term "naturally occurring bile acid" denotes any free or conjugated bile acid occurring in man such as cholic acid, deoxycholic acid, chenodeoxycholic acid, glycocholic acid, etc.

DETAILED DESCRIPTION OF THE PREFERRED EMBODIMENTS

While all the compounds encompassed within the above generic formulae meet the present inventor's criteria, nevertheless, certain compounds remain preferred as set out below. Additional preferred compounds can be found in the examples which follow:
(1) n-Octanoyloxymethylpyridinium chloride.
(2) n-Dodecanoyloxymethylpyridinium chloride.
(3) n-Tetradecanoyloxymethylpyridinium chloride.
(4) n-Hexadecanoyloxymethylpyridinium chloride.
(5) 1-n-Dodecanoyloxymethyl-3-methylimidazolium chloride.
(6) 1-n-Tetradecanoyloxymethyl-3-methylimidazolium chloride.
(7) 1-n-Hexadecanoyloxymethyl-3-methylimidazolium chloride.
(8) n-Dodecanoyloxymethyltriethylammonium chloride.
(9) 1-n-Dodecanoyloxymethyl-1,4-diazabicyclo [2.2.2] octane chloride.
(10) 1-n-Dodecanoyloxymethyl-N-ethylnicotinamide chloride.
(11) n-Octanoyloxymethyl-3-methylimidazolium chloride or bromide.
(12) n-Octanoyloxymethyl-trimethylammonium chloride or bromide.
(13) n-Octanoyloxymethyl-nicotinamide chloride or bromide.
(14) 1-n-Octanoyloxymethyl-ethylnicotinate chloride or bromide.
(15) 1-n-Octanoyloxymethyl-methylnicotinate chloride or bromide.
(16) n-Octanoyloxymethyl-triethylammonium chloride or bromide.
(17) n-Decanoyloxymethyl-3-methylimidazolium chloride or bromide.
(18) 1-n-Decanoyloxymethyl-pyridinium chloride or bromide.
(19) n-Decanoyloxymethyl-trimethylammonium chloride or bromide.
(20) n-Decanoyloxymethyl-triethylammonium chloride or bromide.
(21) 1-n-Decanoyloxymethyl-nicotinamide chloride or bromide.
(22) 1-n-Decanoyloxymethyl-ethylnicotinate chloride or bromide.
(23) n-Dodecanoyloxymethyl triethylammonium chloride or bromide.
(24) n-Tetradecanoyloxymethyl-trimethylammonium chloride or bromide.
(25) n-Tetradecanoyloxymethyl-triethylammonium chloride or bromide.
(26) 1-n-Tetradecanoyloxymethyl-nicotinamide chloride or bromide.
(27) 1-n-Tetradecanoyloxymethyl-ethylnicotinate chloride or bromide.
(28) 1-n-Tetradecanoyloxymethyl-methylnicotinate chloride or bromide.
(29) 1-n-Tetradecanoyloxymethyl-3-methylimidazolium chloride or bromide.
(30) n-Tetradecanoyloxymethyl-1,4-diazabicyclo [2.2.2] octane chloride or bromide.
(31) 1-[α-(n-Octanoyloxy)ethyl]-pyridinium chloride or bromide.
(32) 1-[α-(n-Octanoyloxy)ethyl]-3-methylimidazolium chloride or bromide.
(33) α-(n-Octanoyloxy)ethyl-trimethylammonium chloride or bromide.
(34) 1-[α-(n-Octanoyloxy)ethyl]-nicotinamide chloride or bromide.
(35) 1-[α-(n-Octanoyloxy)ethyl]-N-ethylnicotinamide chloride or bromide.
(36) 1-[α-(n-Octanoyloxy)ethyl]-ethylnicotinate chloride or bromide.
(37) 1-[α-(n-Decanoyloxy)ethyl]-pyridinium chloride or bromide.
(38) 1-[α-(n-Decanoyloxy)ethyl]-3-methylimidazolium chloride or bromide.
(39) α-(n-Decanoyloxy)ethyl-trimethylammonium chloride or bromide.
(40) α-(n-Decanoyloxy)ethyl-triethylammonium chloride or bromide.

(41) 1-[α-(n-Decanoyloxy)ethyl]-nicotinamide chloride or bromide.
(42) 1-[α-(n-Decanoyloxy)ethyl]-N-ethylnicotinamide chloride or bromide.
(43) 1-[α-(n-Decanoyloxy)ethyl]-ethylnicotinate chloride or bromide.
(44) 1-[α-(n-Decanoyloxy)ethyl]-1,4-diazabicyclo[2.2.2] octane chloride or bromide.
(45) 1-[α-(n-Dodecanoyloxy)ethyl]-pyridinium chloride or bromide.
(46) α-(n-Dodecanoyloxy)ethyl-trimethylammonium chloride or bromide. (47) α-(n-Dodecanoyloxy)ethyl-trimethylammonium chloride or bromide.
(48) 1-[α-(n-Dodecanoyloxy)ethyl]-nicotinamide chloride or bromide.
(49) 1-[α-(n-Dodecanoyloxy)ethyl]-3-methylimidazolium chloride or bromide.
(50) 1-[α-(n-Dodecanoyloxy)ethyl]-N-ethylnicotinamide chloride or bromide.
(51) 1-[α-(n-Hexadecanoyloxy)ethyl]-pyridinium chloride or bromide.
(52) α-(n-Hexadecanoyloxy)ethyl-trimethylammonium chloride or bromide.
(53) α-(n-Hexadecanoyloxy)ethyl-triethylammonium chloride or bromide.
(54) 1-[α-(n-Hexadecanoyloxy)ethyl]-nicotinamide chloride or bromide.
(55) 1-[α-(n-Hexadecanoyloxy)ethyl]-3-methylimidazolium chloride or bromide.
(56) 1-[α-(n-Hexadecanoyloxy)ethyl]-N-ethylnicotinamide chloride or bromide.
(57) 1-[α-(n-Hexadecanoyloxy)ethyl]-ethylnicotinate chloride or bromide.
(58) 1-Oleyloxymethyl-pyridinium chloride or bromide.
(59) Oleyloxymethyl-trimethylammonium chloride or bromide.
(60) Oleyloxymethyl-triethylammonium chloride or bromide.
(61) 1-Oleyloxymethyl-nicotinamide chloride or bromide.
(62) 1-Oleyloxymethyl-N-ethylnicotinamide chloride or bromide.
(63) 1-Oleyloxymethyl-ethylnicotinate chloride or bromide.
(64) 1-Oleyloxymethyl-3-methylimidazolium chloride or bromide.

As can be determined from the examples which follow, depending on the spectrum of bacteria treated, one and/or mixtures of two or more of the above-described compounds may be employed.

At this point, it should be strictly emphasized that when the substituent $R_1$ in formula (I) represents a $C_0$–$C_{22}$ straight or branched

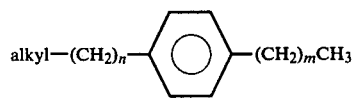

group or an

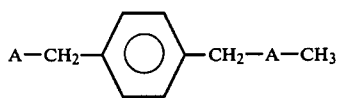

the art which can be added to or substituted for the benzene ring in either one of the above long chain moieties for the purpose of improving their surface active properties may also be introduced. Typically, and without limitation, a pyridyl, a thiazolyl, an imidazolyl, or naphthyl function are illustrative.

The compounds of the present invention can be conveniently prepared in the manner described below:

METHOD "A"

React an α-halo-ester of the general formula:

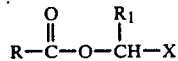

wherein R, $R_1$ and X are defined as above, directly with a tertiary aliphatic amine (≫N) or an unsaturated amine (≫N) in approximately equimolecular proportion, in the presence of an inert solvent (ether, acetonitrile, $CH_2Cl_2$, etc.) at room temperature or at the reflux temperature of the solvent for 2–24 hours. As an alternative procedure, the above reaction can be carried out in the absence of a solvent by mixing the above two reactants together and maintaining them at room temperature or between 20°–70° C. for 2–24 hours. In both cases, the crystalline salt formed can be purified by crystallization from an ether-ethanol mixture, or the like.

METHOD "B"

The same compounds can be obtained by first mixing the tertiary aliphatic amine (≫N) or unsaturated amine (≫N) with an equimolecular amount of the corresponding acyl halide

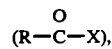

maintaining the mixture at room temperature for 2–24 hours. Then there is added to the reaction mixture an equimolecular amount of the aldehyde ($R_1$—CHO). The mixture is then stirred at room temperature or elevated temperature, up to 75° C., for 2–28 hours. Purification of the final product is carried out as in Method "A".

In the above description of Method "B", R, $R_1$ and X are defined as above.

Without further elaboration, it is believed that one of ordinary skill in the art can, using the preceding description, utilize the present invention to its fullest extent. Consequently, the following preferred specific embodiments are to be construed as merely illustrative and not limitative of the remainder of the specification and claims in any way whatsoever. Reference to temperature means centigrade unless otherwise indicated.

EXAMPLE I

Preparation of Some Selective Compounds of the Present Invention

A series of new chloromethyl n-alkylcarboxylates (1 a–d) were prepared by reaction of the corresponding acyl chloride with paraformaldehyde in the presence of a catalytic amount of anhydrous zinc chloride (SCHEME 1), applying the procedure of R. Adams and E. H. Vollweiler, *J. Amer. Chem. Soc.*, 40, 1732 (1918); H. E. French and R. Adams, ibid, 43, 651 (1921); and L. H. Ulich and R. Adams, ibid, 43, 660 (1921).

SCHEME 1

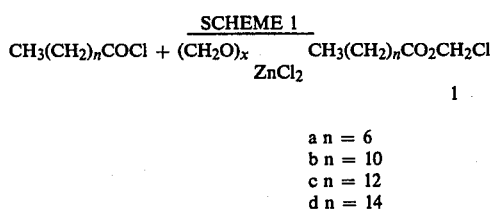

a n = 6
b n = 10
c n = 12
d n = 14

A series of n-alkylcarboxymethyl quaternary salts (2 a–j) were then prepared by reaction of the corresponding chloromethyl n-alkylcarboxylates with an appropriate tertiary amine (SCHEME 2).

SCHEME 2

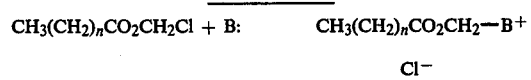

B: = tertiary amine a n = 6, B — Py
b n = 10, B = Py
c n = 12, B = Py
d n = 14, B = Py
e n = 10, B = 1-MeIm[2]
f n = 12, B = 1-MeIm[2]
g n = 14, B = 1-MeIm[2]
h n = 10, B = Et$_3$N
i n = 10, B = DABCO[3]
j n = 10, B =

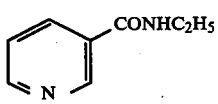

2: 1-MeIm = 1-methylimidazole
3. DABCO = 1,4-diazabicyclo [2.2.2]octane n-Octanoyloxymethylpyridinium chloride (2a)

A mixture of 1.93 g (0.01 mol) chloromethyl n-octanoate (1a) and 0.79 g (0.01 mol) pyridine were mixed and heated together at 90° for 3 hours. On cooling to room temperature, anhydrous ether was added to the mixture and the mixture was triturated in anhydrous ether overnight. The solid was isolated by filtration under a nitrogen atmosphere and thoroughly washed with anhydrous ether. After drying in vacuo over calcium sulfate at room temperature, 1.90 g (0.007 mol), 70%, 2a was obtained as a white solid, mp 102°–107°, ir (KBr) 3430, 3040, 2970, 1770, 1635, 1490, 1110, 760, and 670 cm$^{-1}$; pmr (CDCl$_3$) δ 9.9 (d, 2H), 8.8 (t, 1H), 8.3 (t, 2H), 7.0 (s, 2H) 2.4 (t, 2H), 1.3 (bs, 10H) and 0.9 (bt, 3H) ppm.

Anal. Calcd for C$_{14}$H$_{22}$ClNO$_2$.H$_2$O: C, 58.02; H, 8.35; N, 4.83. Found: C, 57.51; H, 7.76; N, 4.58.

Using the procedure described for the preparation of 2a the following n-alkylcarboxymethyl pyridinium salts were prepared:

n-Dodecanoyloxymethylpyridinium chloride (2b)

mp 120°–124°, ir (KBr) 3430, 3020, 2960, 1770, 1635, 1490, 1470, 1110, 760, and 670 cm$^{-1}$; pmr (CDCl$_3$) δ 9.9 (d, 2H), 8.8 (t, 1H), 8.2 (t, 2H), 7.0 (s, 2H), 2.4 (t, 2H), 1.2 (bs, 18H) and 0.9 (bt, 3H) ppm.

Anal. Calcd for C$_{18}$H$_{30}$ClNO$_2$.H$_2$O: C, 62.50; H, 9.33; N, 4.05. Found: C, 63.54; H, 8.26; H, 3.86.

n-Tetradecanoyloxymethylpyridinium chloride (2c)

mp 104°–109°, ir (KBr) 3420, 3010, 2960, 2920, 1770, 1638, 1485, 1470, 1110, 760 and 670 cm$^{-1}$; pmr (CDCl$_3$) δ 9.9 (d, 2H), 8.8 (t, 1H), 8.3 (t, 2H), 7.0 (s, 2H) 2.4 (t, 2H), 1.3 (bs, 22H), and 0.8 (bt, 3H) ppm.

Anal. Calcd for C$_{20}$H$_{34}$ClNO$_2$.H$_2$O: C, 64.23; H, 9.70; N, 3.75. Found: C, 63.55; H, 9.25; N, 3.60.

n-Hexadecanoyloxymethylpyridinium chloride (2d)

mp 132°–135°, ir (KBr) 3430, 3020, 2970, 2930, 1770, 1635, 1490, 1470, 1110, 760, and 670 cm$^{-1}$; pmr (CDCl$_3$) δ 9.9 (d, 2H), 8.8 (t, 1H), 1.3 (bs, 26H), and 0.9 (bt, 3H) ppm.

Anal. Calcd for C$_{22}$H$_{38}$ClNO$_2$: C, 68.81; H, 9.97; N, 3.65. Found: C, 68.59; H, 9.97; N, 3.60.

1-n-Dodecanoyloxymethyl-3-methylimidazolium chloride (2e)

A mixture of 2.49 g (0.01 mol) chloromethyl n-dodecanoate (2b) and 0.82 g (0.01 mol) 1-methylimidazole were mixed and heated together at 90° for 3 hours. On cooling to room temperature, anhydrous ether was added to the mixture and the mixture was triturated in anhydrous ether overnight. The solid was isolated by filtration under a nitrogen atmosphere and thoroughly washed with anhydrous ether. After drying in vacuo over calcium sulfate at room temperature, 2.4 g (0.007 mol), 70%, 2e was obtained as a white solid, mp 60°–63°, ir (KBr) 3400, 3110, 2960, 2920, 1750, 1470, 1140 and 770 cm$^{-1}$, pmr (CDCl$_3$) δ 10.8 (s, 1H), 8.0 (d, 2H), 6.4 (s, 2H), 4.2 (s, 3H), 2.4 (t, 2H), 1.4 (bs, 18H) and 0.9 (bt, 3H) ppm.

Anal. Calcd for C$_{17}$H$_{31}$ClN$_2$O$_2$.H$_2$O: C, 58.52; H, 9.53; N, 8.03. Found: C, 58.85; H, 9.54; N, 8.79.

Using the procedure described for the preparation of 2e the following n-alkylcarboxymethyl-3-methylimidazolium salts were prepared:

1-n-Tetradecanoyloxymethyl-3-methylimidazolium chloride (2f)

mp 68°–74°, ir (KBr) 3400, 3180, 2960, 2920, 1750, 1470, 1140 and 770 cm$^{-1}$; pmr (CDCl$_3$) δ 10.8 (s, 1H), 8.0 (d, 2H), 6.4 (s, 2H), 4.2 (s, 3H), 2.4 (t, 2H), 1.2 (bs, 22H), and 0.9 (bt, 3H) ppm.

Anal. Calcd for C$_{19}$H$_{35}$ClN$_2$O$_2$.H$_2$O: C, 57.77; H, 9.95; N, 7.38. Found: C, 58.85; H, 9.59; N, 7.38.

1-n-Hexadecanoyloxymethyl-3-methylimidazolium chloride (2g)

mp 80°–84°; ir (KBr) 3410, 3110, 2960, 2925, 1760, 1470, 1140 and 750 cm$^{-1}$; pmr (CDCl$_3$) δ 10.8 (s, 1H), 8.0 (d, 2H), 6.4 (s, 2H), 4.2 (s, 3H), 2.4 (t, 2H), 1.3 (bs, 26H) and 0.9 (bt, 3H) ppm.

Anal. Calcd for C$_{21}$H$_{39}$ClN$_2$O$_2$.H$_2$0: C, 62.27; H, 10.20; N, 6.92. Found: C, 62.13; H, 10.40; N, 7.41.

n-Dodecanoyloxymethyltriethylammonium chloride (2h)

2.49 g (0.01 mol) chloromethyl n-dodecanoate (1b) and 1.01 g (0.01 mol) triethylamine were mixed and heated together at 90° for three hr. On cooling to room temperature, anhydrous ether was added to the mixture and the mixture was triturated in anhydrous ether overnite. The solid was isolated by filtration under a nitrogen atmosphere and thoroughly washed with ether. After drying in vacuo over calcium sulfate at room temperature 0.6 g (0.002 mol 20%, 2h was obtained as a hygroscopic solid, mp 72°–77°.

1-n-Dodecanoyloxymethyl-1,4-diazabicyclo [2.2.2]octane chloride (2i)

2.49 g (0.01 mol) chloromethyl n-dodecanoate and 1.12 g (0.01 mol) 1,4-diazabicyclo [2.2.2]octane were mixed and allowed to react together at room temperature for 72 hr. Anhydrous ether was added to the mixture and the mixture was triturated in anhydrous ether overnite. The solid was isolated by filtration under a nitrogen atmosphere and thoroughly washed with anhydrous ether. After drying in vacuo over calcium sulfate at room temperature, 2.0 g (0.006 mol), 60%, 2i, was obtained as a white solid, mp 106°–110° C., ir (KBr) 3400, 2960, 2920, 1760, 1460, 1120, 1080, 1050, 850 and 830 cm$^{-1}$; pmr (CDCl$_3$) δ 5.8 (s, 2H), 4.2–3.0 (mq, 12H), 2.6 (t, 2H) 1.3 (bs, 18H) and 0.9 (bt, 3H) ppm.

Anal. Calcd for C$_{19}$H$_{37}$ClN$_2$O$_2$·H$_2$O: C, 60.21; H, 10.37; N, 7.39 Found: C, 60.86; H, 10.12; N, 7.68.

1-n-Dodecanoyloxymethyl-N-ethylnicotinamide chloride (2j)

2.49 g (0.01 mol) chloromethyl n-dodecanoate and 1.50 g (0.01 mol) N-ethyl-nicotinamide were mixed and heated together at 90° for 1 hr. On cooling to room temperature, anhydrous ether was added to the mixture and the mixture was triturated in anhydrous ether overnite. The solid was isolated by filtration under a nitrogen atmosphere and thoroughly washed with anhydrous ether. After drying in vacuo over calcium sulfate at room temperature, 2.6 g (0.007 mol), 70%, 2j was obtained as a white solid, mp 131°–135°, ir (KBr) 3220, 3060, 2965, 2930, 1770, 1680, 1640, 1470, 1110 and 670 cm$^{-1}$; pmr (CDCl$_3$) δ 10.5 (s, 1H), 9.8 (m, 3H), 8.3 (t, 1H), 6.8 (s, 2H), 3.6 (q, 2H), 2.5 (t, 2H), 1.3 (bs, 21H) and 0.9 (bt, 3H) ppm.

Anal. Calcd for C$_{21}$H$_{35}$ClN$_2$O$_3$: C, 63.22; H, 8.84; N, 7.02. Found: C, 62.70; H, 8.63; N, 6.90.

By following the preceding example and substituting the generically or specifically described reactants and/or operating conditions of this invention, the following additional compounds can be prepared.

TABLE I $$\diagdown\!\!\!\!\!\underset{\diagup}{\text{N}}^{\oplus}\!\!-\!\!\underset{\underset{\text{H}}{|}}{\text{C}}\!\!-\!\!\text{O}\!\!-\!\!\underset{\underset{\text{O}}{\|}}{\text{C}}\!\!-\!\!\text{R}_1 \ \text{X}^{\ominus}$$

| R | R$_1$ | $\diagdown\!\!\text{N}\!\!\diagup$ | X$^{\ominus}$ |
|---|---|---|---|
| H | CH$_3$(CH$_2$)$_7$— | —N⟨pyrazole⟩NCH$_3$ | Cl$^-$ |
| H | CH$_3$(CH$_2$)$_7$— | N(CH$_3$)$_3$ | Cl$^-$ |
| H | CH$_3$(CH$_2$)$_7$— | N(C$_2$H$_5$)$_3$ | Cl$^-$ |
| H | CH$_3$(CH$_2$)$_7$— | pyridinium-CONH$_2$ | Cl$^-$ |
| H | CH$_3$(CH$_2$)$_7$— | pyridinium-COOC$_2$H$_5$ | Cl$^-$ |
| H | CH$_3$(CH$_2$)$_7$— | pyridinium-COOCH$_3$ | Cl$^-$ |

TABLE I-continued $$\underset{\underset{\underset{N}{\parallel}}{|}}{\overset{R}{\underset{|}{N^{\oplus}-CH-O-C-R_1}}}\ X^{\ominus}$$

| R | R₁ | $\overset{\diagdown}{\underset{\diagup}{N}}$ | X⊖ |
|---|---|---|---|
| H | CH₃(CH₂)₇— | pyridine-3-CONHC₂H₅ | Cl⁻ |
| H | CH₃(CH₂)₇— | quinuclidine | Cl⁻ |
| H | CH₃(CH₂)₈— | N-methylimidazole (NCH₃) | Cl⁻ |
| H | CH₃(CH₂)₈— | N(CH₃)₃ | Cl⁻ |
| H | CH₃(CH₂)₈— | N(C₂H₅)₃ | Cl⁻ |
| H | CH₃(CH₂)₈— | pyridine-3-CONH₂ | Cl⁻ |
| H | CH₃(CH₂)₈— | pyridine-3-COOC₂H₅ | Cl⁻ |
| H | CH₃(CH₂)₈— | pyridine-3-COOCH₃ | Cl⁻ |
| H | CH₃(CH₂)₈— | pyridine-3-CONHC₂H₅ | Cl⁻ |
| H | CH₃(CH₂)₈— | quinuclidine | Cl⁻ |
| H | CH₃(CH₂)₁₀— | N-methylimidazole (NCH₃) | Cl⁻ |
| H | CH₃(CH₂)₁₀— | N(CH₃)₃ | Cl⁻ |

TABLE I-continued $$-\overset{R}{\underset{|}{N^\oplus}}-\overset{|}{\underset{|}{CH}}-O-\overset{O}{\underset{||}{C}}-R_1 \ X^\ominus$$

| R | R₁ | $\overset{|}{\underset{|}{N}}$ | X⁻ |
|---|---|---|---|
| H | CH₃(CH₂)₁₀— | N(C₂H₅)₃ | Cl⁻ |
| H | CH₃(CH₂)₁₀— | 3-carbamoylpyridinyl (CONH₂) | Cl⁻ |
| H | CH₃(CH₂)₁₀— | 3-(ethoxycarbonyl)pyridinyl (COOC₂H₅) | Cl⁻ |
| H | CH₃(CH₂)₁₀— | 3-(methoxycarbonyl)pyridinyl (COOCH₃) | Cl⁻ |
| H | CH₃(CH₂)₁₀— | 3-(N-ethylcarbamoyl)pyridinyl (CONHC₂H₅) | Cl⁻ |
| H | CH₃(CH₂)₁₀— | quinuclidinyl | Cl⁻ |
| H | CH₃(CH₂)₁₂— | 1-methylimidazolyl | Cl⁻ |
| H | CH₃(CH₂)₁₂— | N(CH₃)₃ | Cl⁻ |
| H | CH₃(CH₂)₁₂— | N(C₂H₅)₃ | Cl⁻ |
| H | CH₃(CH₂)₁₂— | 3-carbamoylpyridinyl (CONH₂) | Cl⁻ |
| H | CH₃(CH₂)₁₂— | 3-(ethoxycarbonyl)pyridinyl (COOC₂H₅) | Cl⁻ |

TABLE I-continued $$\diagup N^{\oplus}\overset{R}{\underset{|}{-}}CH-O-\overset{O}{\underset{\|}{C}}-R_1 \quad X^{\ominus}$$

| R | R$_1$ | $\diagdown N \diagup$ | X$^\ominus$ |
|---|---|---|---|
| H | CH$_3$(CH$_2$)$_{12}$— | 3-pyridyl-COOCH$_3$ | Cl$^-$ |
| H | CH$_3$(CH$_2$)$_{12}$— | 3-pyridyl-CONHC$_2$H$_5$ | Cl$^-$ |
| H | CH$_3$(CH$_2$)$_{12}$— | quinuclidinyl | Cl$^-$ |
| H | CH$_3$(CH$_2$)$_{13}$— | N-methylimidazolyl | Cl$^-$ |
| H | CH$_3$(CH$_2$)$_{13}$— | N(CH$_3$)$_3$ | Cl$^-$ |
| H | CH$_3$(CH$_2$)$_{13}$— | N(C$_2$H$_5$)$_3$ | Cl$^-$ |
| H | CH$_3$(CH$_2$)$_{13}$— | 3-pyridyl-CONH$_2$ | Cl$^-$ |
| H | CH$_3$(CH$_2$)$_{13}$— | 3-pyridyl-COOC$_2$H$_5$ | Cl$^-$ |
| H | CH$_3$(CH$_2$)$_{13}$— | 3-pyridyl-COOCH$_3$ | Cl$^-$ |
| H | CH$_3$(CH$_2$)$_{13}$— | 3-pyridyl-CONHC$_2$H$_5$ | Cl$^-$ |
| H | CH$_3$(CH$_2$)$_{13}$— | quinuclidinyl | Cl$^-$ |

TABLE I-continued $$\diagup N^{\oplus}-\underset{R}{\overset{R}{C}}H-O-\overset{O}{\overset{\|}{C}}-R_1 \ X^{\ominus}$$

| R | R₁ | (heterocycle/amine group) | X⁻ |
|---|---|---|---|
| H | $CH_3(CH_2)_{14}-$ | imidazole-N-CH₃ | Cl⁻ |
| H | $CH_3(CH_2)_{14}-$ | $N(CH_3)_3$ | Cl⁻ |
| H | $CH_3(CH_2)_{14}-$ | $N(C_2H_5)_3$ | Cl⁻ |
| H | $CH_3(CH_2)_{14}-$ | pyridine-CONH₂ | Cl⁻ |
| H | $CH_3(CH_2)_{14}-$ | pyridine-COOC₂H₅ | Cl⁻ |
| H | $CH_3(CH_2)_{14}-$ | pyridine-COOCH₃ | Cl⁻ |
| H | $CH_3(CH_2)_{14}-$ | pyridine-CONHC₂H₅ | Cl⁻ |
| H | $CH_3(CH_2)_{14}-$ | quinuclidine | Cl⁻ |
| CH₃ | $CH_3(CH_2)_{7}-$ | imidazole-N-CH₃ | Cl⁻ |
| CH₃ | $CH_3(CH_2)_{7}-$ | $N(CH_3)_3$ | Cl⁻ |
| CH₃ | $CH_3(CH_2)_{7}-$ | $N(C_2H_5)_3$ | Cl⁻ |
| CH₃ | $CH_3(CH_2)_{7}-$ | pyridine-CONH₂ | Cl⁻ |

TABLE I-continued $$-\overset{|}{\underset{|}{N}}{}^{\oplus}-\overset{R}{\underset{|}{C}}H-O-\overset{O}{\underset{}{C}}-R_1 \; X^{\ominus}$$

| R | $R_1$ | $\overset{|}{\underset{|}{N}}$ | $X^{\ominus}$ |
|---|---|---|---|
| $CH_3$ | $CH_3(CH_2)_7-$ | 3-pyridyl-COOC$_2$H$_5$ | $Cl^-$ |
| $CH_3$ | $CH_3(CH_2)_7-$ | 3-pyridyl-COOCH$_3$ | $Cl^-$ |
| $CH_3$ | $CH_3(CH_2)_7-$ | 3-pyridyl-CONHC$_2$H$_5$ | $Cl^-$ |
| $CH_3$ | $CH_3(CH_2)_7-$ | quinuclidinyl | $Cl^-$ |
| $CH_3$ | $CH_3(CH_2)_8-$ | 1-methylimidazol-2-yl | $Cl^-$ |
| $CH_3$ | $CH_3(CH_2)_8-$ | $-N(CH_3)_3$ | $Cl^-$ |
| $CH_3$ | $CH_3(CH_2)_8-$ | $-N(C_2H_5)_3$ | $Cl^-$ |
| $CH_3$ | $CH_3(CH_2)_8-$ | 3-pyridyl-CONH$_2$ | $Cl^-$ |
| $CH_3$ | $CH_3(CH_2)_8-$ | 3-pyridyl-COOC$_2$H$_5$ | $Cl^-$ |
| $CH_3$ | $CH_3(CH_2)_8-$ | 3-pyridyl-COOCH$_3$ | $Cl^-$ |
| $CH_3$ | $CH_3(CH_2)_8-$ | 3-pyridyl-CONHC$_2$H$_5$ | $Cl^-$ |

TABLE I-continued $$\diagdown_{N^{\oplus}}\!\!\!-\!\!\overset{R}{\underset{}{C}H}\!\!-\!\!O\!\!-\!\!\overset{O}{\underset{}{C}}\!\!-\!\!R_1\ X^{\ominus}$$

| R | R₁ | [substituent] | X⁻ |
|---|---|---|---|
| CH₃ | CH₃(CH₂)₈— | 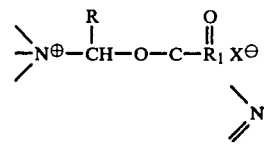 | Cl⁻ |
| CH₃ | CH₃(CH₂)₁₀— |  | Cl⁻ |
| CH₃ | CH₃(CH₂)₁₀— |  | Cl⁻ |
| CH₃ | CH₃(CH₂)₁₀— |  | Cl⁻ |
| CH₃ | CH₃(CH₂)₁₀— | 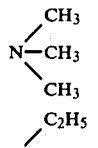 | Cl⁻ |
| CH₃ | CH₃(CH₂)₁₀— | 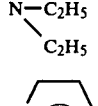 | Cl⁻ |
| CH₃ | CH₃(CH₂)₁₀— |  | Cl⁻ |
| CH₃ | CH₃(CH₂)₁₀— | 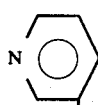 | Cl⁻ |
| CH₃ | CH₃(CH₂)₁₀— | 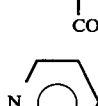 | Cl⁻ |
| CH₃ | CH₃(CH₂)₁₂— | 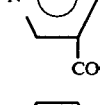 | Cl⁻ |
| CH₃ | CH₃(CH₂)₁₂— | 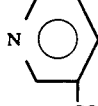 | Cl⁻ |
| CH₃ | CH₃(CH₂)₁₂— | 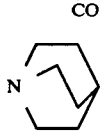 | Cl⁻ |

TABLE I-continued $$\begin{array}{c}\diagdown\\ \diagup\end{array}\!\!N^{\oplus}\!\!-\!\!\overset{R}{\underset{}{C}H}\!\!-\!\!O\!\!-\!\!\overset{O}{\underset{}{C}}\!\!-\!\!R_1\ X^{\ominus}$$

| R | $R_1$ | $\diagdown N \diagup$ | $X^{\ominus}$ |
|---|---|---|---|
| $CH_3$ | $CH_3(CH_2)_{12}-$ | 3-pyridyl-CONH$_2$ | $Cl^-$ |
| $CH_3$ | $CH_3(CH_2)_{12}-$ | 3-pyridyl-COOC$_2$H$_5$ | $Cl^-$ |
| $CH_3$ | $CH_3(CH_2)_{12}-$ | 3-pyridyl-COOCH$_3$ | $Cl^-$ |
| $CH_3$ | $CH_3(CH_2)_{12}-$ | 3-pyridyl-CONHC$_2$H$_5$ | $Cl^-$ |
| $CH_3$ | $CH_3(CH_2)_{12}-$ | quinuclidinyl | $Cl^-$ |
| $CH_3$ | $CH_3(CH_2)_{13}-$ | N-methylimidazolyl (NCH$_3$) | $Cl^-$ |
| $CH_3$ | $CH_3(CH_2)_{13}-$ | $N(CH_3)_3$ | $Cl^-$ |
| $CH_3$ | $CH_3(CH_2)_{13}-$ | $N(C_2H_5)_3$ | $Cl^-$ |
| $CH_3$ | $CH_3(CH_2)_{13}-$ | 3-pyridyl-CONH$_2$ | $Cl^-$ |
| $CH_3$ | $CH_3(CH_2)_{13}-$ | 3-pyridyl-COOC$_2$H$_5$ | $Cl^-$ |
| $CH_3$ | $CH_3(CH_2)_{13}-$ | 3-pyridyl-COOCH$_3$ | $Cl^-$ |

TABLE I-continued $$-\underset{|}{\overset{|}{N}}{}^{\oplus}-\underset{\underset{R}{|}}{CH}-O-\overset{\overset{O}{\|}}{C}-R_1 \quad X^{\ominus}$$

| R | $R_1$ | $\diagdown N \diagup$ | $X^{\ominus}$ |
|---|---|---|---|
| $CH_3$ | $CH_3(CH_2)_{13}-$ | 3-(N-ethylcarbamoyl)pyridinyl | $Cl^-$ |
| $CH_3$ | $CH_3(CH_2)_{13}-$ | quinuclidinyl | $Cl^-$ |
| $CH_3$ | $CH_3(CH_2)_{14}-$ | 3-methylimidazolyl | $Cl^-$ |
| $CH_3$ | $CH_3(CH_2)_{14}-$ | trimethylammoniomethyl | $Cl^-$ |
| $CH_3$ | $CH_3(CH_2)_{14}-$ | triethylammoniomethyl | $Cl^-$ |
| $CH_3$ | $CH_3(CH_2)_{14}-$ | 3-carbamoylpyridinyl | $Cl^-$ |
| $CH_3$ | $CH_3(CH_2)_{14}-$ | 3-(ethoxycarbonyl)pyridinyl | $Cl^-$ |
| $CH_3$ | $CH_3(CH_2)_{14}-$ | 3-(methoxycarbonyl)pyridinyl | $Cl^-$ |
| $CH_3$ | $CH_3(CH_2)_{14}-$ | 3-(N-ethylcarbamoyl)pyridinyl | $Cl^-$ |
| $CH_3$ | $CH_3(CH_2)_{14}-$ | quinuclidinyl | $Cl^-$ |
| H | $CH_3-\underset{\underset{CH_3}{\mid}}{\overset{\overset{CH_3}{\mid}}{C}}-CH_2-\underset{\underset{CH_3}{\mid}}{\overset{\overset{CH_3}{\mid}}{C}}-C_6H_4-CH_2-$ | 3-methylimidazolyl | $Cl^-$ |
| H | $CH_3-\underset{\underset{CH_3}{\mid}}{\overset{\overset{CH_3}{\mid}}{C}}-CH_2-\underset{\underset{CH_3}{\mid}}{\overset{\overset{CH_3}{\mid}}{C}}-C_6H_4-CH_2-$ | trimethylammoniomethyl | $Cl^-$ |

TABLE I-continued $$-N^{\oplus}\underset{|}{\overset{R}{C}}H-O-C-\underset{\|}{\overset{O}{C}}-R_1\ X^{\ominus}$$

| R | $R_1$ | $\overset{\diagdown}{\underset{\diagup}{N-}}$ | $X^{\ominus}$ |
|---|---|---|---|
| H | $CH_3-\underset{\underset{CH_3}{\|}}{\overset{\overset{CH_3}{\|}}{C}}-CH_2-\underset{\underset{CH_3}{\|}}{\overset{\overset{CH_3}{\|}}{C}}-\underset{}{\bigcirc}-CH_2-$ | $N\underset{\diagdown C_2H_5}{\overset{\diagup C_2H_5}{-C_2H_5}}$ | $Cl^-$ |
| H | $CH_3-\underset{\underset{CH_3}{\|}}{\overset{\overset{CH_3}{\|}}{C}}-CH_2-\underset{\underset{CH_3}{\|}}{\overset{\overset{CH_3}{\|}}{C}}-\bigcirc-CH_2-$ | pyridyl-CONH$_2$ | $Cl^-$ |
| H | $CH_3-\underset{\underset{CH_3}{\|}}{\overset{\overset{CH_3}{\|}}{C}}-CH_2-\underset{\underset{CH_3}{\|}}{\overset{\overset{CH_3}{\|}}{C}}-\bigcirc-CH_2-$ | pyridyl-COOC$_2$H$_5$ | $Cl^-$ |
| H | $CH_3-\underset{\underset{CH_3}{\|}}{\overset{\overset{CH_3}{\|}}{C}}-CH_2-\underset{\underset{CH_3}{\|}}{\overset{\overset{CH_3}{\|}}{C}}-\bigcirc-CH_2-$ | pyridyl-COOCH$_3$ | $Cl^-$ |
| H | $CH_3-\underset{\underset{CH_3}{\|}}{\overset{\overset{CH_3}{\|}}{C}}-CH_2-\underset{\underset{CH_3}{\|}}{\overset{\overset{CH_3}{\|}}{C}}-\bigcirc-CH_2-$ | pyridyl-CONHC$_2$H$_5$ | $Cl^-$ |
| H | $CH_3-\underset{\underset{CH_3}{\|}}{\overset{\overset{CH_3}{\|}}{C}}-CH_2-\underset{\underset{CH_3}{\|}}{\overset{\overset{CH_3}{\|}}{C}}-\bigcirc-CH_2-$ | pyrrolidinyl | $Cl^-$ |
| $CH_3O-CH_2-CH_2-$ | $CH_3(CH_2)_{11}-$ | Pyridine | $Cl^-$ |
| $CH_3O-CH_2-CH_2-$ | $CH_3(CH_2)_{11}$ | $(CH_3)_3N$ | $Cl^-$ |
| $CH_3O-CH_2-CH_2-$ | $CH_3(CH_2)_{11}-$ | $(C_2H_5)_3N$ | $Cl^-$ |
| $CH_3O-CH_2-CH_2-$ | $CH_3(CH_2)_{11}-$ | pyridyl-CONHC$_2$H$_5$ | $Cl^-$ |
| $CH_3OOC-CH_2-CH_2-$ | $CH_3(CH_2)_{11}-$ | Pyridine | $Cl^-$ |
| $CH_3OOC-CH_2-CH_2-$ | $CH_3CH_2)_{11}-$ | $(CH_3)_3N$ | $Cl^-$ |
| $CH_3OOC-CH_2-CH_2-$ | $CH_3(CH_2)_{11}-$ | $(C_2H_5)_3N$ | $Cl^-$ |
| $CH_3OOC-CH_2-CH_2-$ | $CH_3(CH_2)_{11}-$ | pyridyl-CONHC$_2$H$_5$ | $Cl^-$ |
| $HOOC-CH_2CH_2-$ | $CH_3(CH_2)_{11}-$ | Pyridine | $Cl^-$ |
| $HOOC-CH_2CH_2-$ | $CH_3(CH_2)_{11}-$ | $(CH_3)_3N$ | $Cl^-$ |
| $HOOC-CH_2CH_2-$ | $CH_3(CH_2)_{11}-$ | $(C_2H_5)_3N$ | $Cl^-$ |
| $HOOC-CH_2CH_2-$ | $CH_3(CH_2)_{11}-$ | pyridyl-CONHC$_2$H$_5$ | $Cl^-$ |

TABLE I-continued $$\diagdown N^{\oplus}-\overset{R}{\underset{|}{CH}}-O-\overset{O}{\underset{\|}{C}}-R_1 \ X^{\ominus}$$

| R | $R_1$ | $\diagdown N \diagup$ | $X^{\ominus}$ |
|---|---|---|---|
| 4-CH₃O-C₆H₄- | CH₃(CH₂)₁₁- | Pyridine | Cl⁻ |
| 4-CH₃O-C₆H₄- | CH₃(CH₂)₁₁- | (CH₃)₃N | Cl⁻ |
| 4-CH₃O-C₆H₄- | CH₃(CH₂)₁₁- | (C₂H₅)₃N | Cl⁻ |
| 4-CH₃O-C₆H₄- | CH₃(CH₂)₁₁- | 3-(CONHC₂H₅)-Pyridine | Cl⁻ |
| 4-HOOC-C₆H₄- | CH₃(CH₂)₁₁- | Pyridine | Cl⁻ |
| 4-HOOC-C₆H₄- | CH₃(CH₂)₁₁- | (CH₃)₃N | Cl⁻ |
| 4-HOOC-C₆H₄- | CH₃(CH₂)₁₁- | (C₂H₅)₃N | Cl⁻ |
| 4-HOOC-C₆H₄- | CH₃(CH₂)₁₁- | 3-(CONHC₂H₅)-Pyridine | Cl⁻ |
| 4-C₂H₅OCOO-C₆H₄- | CH₃(CH₂)₁₁- | Pyridine | Cl⁻ |
| 4-C₂H₅OCOO-C₆H₄- | CH₃(CH₂)₁₁- | (CH₃)₃N | Cl⁻ |
| 4-C₂H₅OCOO-C₆H₄- | CH₃(CH₂)₁₁- | (C₂H₅)₃N | Cl⁻ |
| 4-C₂H₅OCOO-C₆H₄- | CH₃(CH₂)₁₁- | 3-(CONHC₂H₅)-Pyridine | Cl⁻ |
| H | (CH₃)₃C-CH(CH₃)-CH₂-CH(CH₃)-CH₂-CH₂- | Pyridine | Cl⁻ |

TABLE I-continued $$-\overset{R}{\underset{|}{N}}{}^{\oplus}-CH-O-\overset{O}{\underset{\|}{C}}-R_1 \ X^{\ominus}$$

| R | R₁ | $-N\overset{}{\diagdown}$ | $X^{\ominus}$ |
|---|---|---|---|
| H | CH₃-C(CH₃)(CH₃)-CH₂-C(CH₃)(H)-CH₂-C(CH₃)(CH₃)-CH₂- | (CH₃)₃N | Cl⁻ |
| H | CH₃-C(CH₃)(CH₃)-CH₂-C(CH₃)(H)-CH₂-C(CH₃)(CH₃)-CH₂- | (C₂H₅)₃N | Cl⁻ |
| H | CH₃-C(CH₃)(CH₃)-CH₂-C(CH₃)(H)-CH₂-C(CH₃)(CH₃)-CH₂- | Pyridine-CONHC₂H₅ | Cl⁻ |
| H | (CH₃)₂N—(CH₂)₁₁— | Pyridine | Cl⁻ |
| H | (CH₃)₂N—(CH₂)₁₁— | (CH₃)₃N | Cl⁻ |
| H | (CH₃)₂N—(CH₂)₁₁— | (C₂H₅)₃N | Cl⁻ |
| H | (CH₃)₂N—(CH₂)₁₁— | Pyridine-CONHC₂H₅ | Cl⁻ |
| H | (CH₃)₂—N—CO—(CH₂)₁₁— | Pyridine | Cl⁻ |
| H | (CH₃)₂—N—CO—(CH₂)₁₁— | (CH₃)₃N | Cl⁻ |
| H | (CH₃)₂—N—CO—(CH₂)₁₁— | (C₂H₅)₃N | Cl⁻ |
| H | (CH₃)₂—N—CO—(CH₂)₁₁— | Pyridine-CONHC₂H₅ | Cl⁻ |
| H | CH₂(CH₂)₃—C₆H₄—(CH₂)₅— | Pyridine | Cl⁻ |
| H | CH₂(CH₂)₃—C₆H₄—(CH₂)₅— | (CH₃)₃N | Cl⁻ |
| H | CH₂(CH₂)₃—C₆H₄—(CH₂)₅— | (C₂H₅)₃N | Cl⁻ |
| H | CH₂(CH₂)₃—C₆H₄—(CH₂)₅— | Pyridine-CONHC₂H₅ | Cl⁻ |
| H | (CH₃)₃C—CH₂—C(CH₃)₂—C₆H₄—O—CH₂CH₂—O—CH₂CH₂—O—CH₂— | | |

TABLE I-continued $$\begin{array}{c} R \\ | \\ -N^{\oplus}-CH-O-C-R_1 \ X^{\ominus} \\ | \quad\quad\quad \| \\ \quad\quad\quad O \end{array}$$

| R | R₁ | $\overset{\diagdown}{\underset{\diagup}{N}}$ | X⁻ |
|---|---|---|---|
| H | CH₃−C(O)−CH₂−C(CH₃)₂−C₆H₄−O−CH₂CH₂−O−CH₂CH₂−O−CH₂− (with CH₃ groups on C) | (CH₃)₃N | Cl⁻ |
| H | CH₃−C(O)−CH₂−C(CH₃)₂−C₆H₄−O−CH₂CH₂−O−CH₂CH₂−O−CH₂− (with CH₃ groups on C) | (C₂H₅)₃N | Cl⁻ |
| H | CH₃−C(O)−CH₂−C(CH₃)₂−C₆H₄−O−CH₂CH₂−O−CH₂CH₂−O−CH₂− (with CH₃ groups on C) | pyridine with CONHC₂H₅ | Cl⁻ |
| H | (cholic acid residue) | Pyridine | Cl⁻ |
| H | (cholic acid residue) | (CH₃)₃N | Cl⁻ |
| H | (cholic acid residue) | (C₂H₅)₃N | Cl⁻ |
| H | (cholic acid residue) | pyridine with CONHC₂H₅ | Cl⁻ |

EXAMPLE II

Comparative Minimal Inhibitory Concentrations (PPM)$^a$

In the table set out below there is disclosed the minimal inhibitory concentrations (MIC) for certain selective compounds of the instant invention (Compounds 3-8); a corresponding short chain "soft" quaternary surface active agent (Compound 2); and a "hard" quaternary surface active agent of the prior art (cetylpyridinium chloride, Compound 1). All MIC values were determined by standard MIC determinative techniques.

TABLE II

| | COMPOUND | S. aureus | B. subtilis | S. typhimirum | P. aeruginosa | S. pyogenes |
|---|---|---|---|---|---|---|
| (1) | $CH_3(CH_2)_{15}Py^+Cl^-$ | <2.0 | <2.0 | 8.0 | 16.0 | <2.0 |
| (2) | $CH_3(CH_2)_6CO_2CH_2Py^+Cl^-$* | 529.1 | 529.1 | 1058.2 | 1058.2 | 529.1 |
| (3) | $CH_3(CH_2)_{10}CO_2CH_2Py^+Cl^-$ | 8.9 | 143.1 | 35.8 | <2.2 | 71.5 |
| (4) | $CH_3(CH_2)_{12}CO_2CH_2Py^+Cl^-$ | 8.1 | 8.3 | 133.0 | >1063.9 | 4.2 |
| (5) | $CH_3(CH_2)_{14}CO_2CH_2Py^+Cl^-$ | 16.7 | 1071.1 | 1071.1 | 1071.1 | 267.5 |
| (6) | $CH_3(CH_2)_{10}CO_2CH_2-\overset{+}{N}\diagup\!\!\!\diagdown NCH_3 \ Cl^-$ | 4.1 | 16.3 | 65.3 | 261.2 | 2.0 |
| (7) | $CH_3(CH_2)_{12}CO_2CH_2-\overset{+}{N}\diagup\!\!\!\diagdown NCH_3 \ Cl^-$ | <2.2 | 4.4 | 69.7 | >1115.1 | >2.2 |
| (8) | $CH_3(CH_2)_{14}CO_2CH_2-\overset{+}{N}\diagup\!\!\!\diagdown NCH_3 \ Cl^-$ | 1.3 | >42.4$^b$ | >42.4$^b$ | >42.4$^b$ | >42.4$^b$ |

$^a$Minimal inhibitory concentration determined by standard techniques in 0.1 M $NaH_2PO_4$, pH 7.0.
$^b$Approximately the saturated solubility.
*U.S. Pat. Application, Ser. No. 482,513-Bodor.

EXAMPLE II

IP and IV Toxicity of an Exemplary "Soft" Compound of this Invention Versus Cetylpyridinium Chloride As stated at the outset of the instant application, the uniqueness of the compounds of the present invention resides in their ability to exhibit sufficient antibacterial activity without attendant toxicity. That is, the compounds of the present invention being "soft" in nature will degrade into nontoxic by-products following release of their antibacterial activity.

In support of the above statement, the lethal dose 50 (LD$_{50}$) of a selective compound of the present invention (IRx-1229) was determined via the intraperitoneal (IP) and intravenous (IV) routes The procedure employed and the results obtained are set out below.

Intraperitoneal (IP) Lethal Dose 50
Compound: IRx-1229

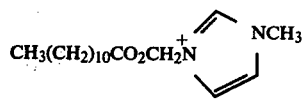

Animal: White Swiss MCR-ICR Mice
Procedure:

The compound was weighed into a 25 ml glass-stoppered flask and dissolved in 10.0 ml 0.9% NaCl, pH 7.0. Each mouse was weighed individually, and 0.01 ml of solution injected per gram of mouse body weight.

Symptoms:
In order of occurrence after injection:
(1) Lack of movement;
(2) Fur stringy and yellow;
(3) Swelling of abdomen;
(4) Trembling;
(5) Eyes irritated and shut;
(6) Darkening and paralysis of extremities; hind legs most noticeable.

Acute Toxicity (Toxicity in 24 hours):
LD$_{50}$(IP) Between 140 mg/kg and 160 mg/kg

TABLE III

| DOSE (mg/kg) | MORTALITY 24 HRS. | Day 1 | Day 2 | Day 3 | Day 4 | Day 5 | Day 6 | Day 7 | MORTALITY 7 DAYS |
|---|---|---|---|---|---|---|---|---|---|
| | | | | | DEATHS PER DAY | | | | |
| 10.00 | 0.4 | — | — | — | — | — | — | — | 0/4 |
| 27.72 | 0.4 | — | — | — | 1 | — | — | — | ¼ |
| 103.10 | 0.4 | — | — | 2 | — | — | 1 | — | ¾ |
| 139.38 | 3/20 | 3 | — | 4 | 2 | 4 | 3 | 3 | 19/20 |
| 148.23 | 6/10 | 6 | — | 1 | 1 | — | — | — | 8/10 |
| 155.09 | 6/10 | 6 | — | 1 | 2 | — | — | — | 9/10 |
| 160.36 | 3/10 | 3 | — | 3 | — | 2 | — | — | 8/10 |
| 166.20 | 8/10 | 8 | 1 | — | — | 1 | — | — | 10/10 |
| 200.00 | ¾ | 3 | — | 1 | — | — | — | — | 4/4 |
| 305.66 | 4/4 | 4 | — | — | — | — | — | — | 4/4 |
| NaCl Control | 0/4 | — | — | — | — | — | — | — | 0/4 |

Intravenous (IV) Lethal Dose 50
Compound: IRx-1229

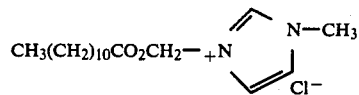

Animal: MCR-ICR White Swiss Male Mice Average Weight 25 grams

Procedure:

The compound was weighed into a 10.0 ml glass beaker and dissolved in varying amounts of 0.9% NaCl, pH 7.0. Each mouse was weighed individually, and injected with varying amounts of solution per gram of body weight. A 50 μl syringe with a 27 gauge needle was used.

Symptoms:

Death either occurred immediately after injection or several day later, never between 5 minutes and 24 hours after injection. When death occurred immediately following injection, it was due to circulatory collapse because of too large an injection or precipitation of the compound in the bloodstream. The death was preceded by convulsions.

All mice that survived the first 24 hrs. began to show severe necrosis of the tail, and by 7 days many mice had lost all or part of their tail.

Acute Toxicity (Toxicity in 24 hours):

$LD_{50}(IV)$ Preliminary study between 100 mg/kg and 133.0 mg/kg

TABLE IV

RESULTS: PRELIMINARY $LD_{50}(IV)$ STUDIES

| DOSE (mg/kg) | INJECTION CONDITIONS | MORTALITY 24 HRS. | MORTALITY 7 DAYS |
|---|---|---|---|
| 35.09 | 175.45 mg/5.0 ml 1.00 μl/gram | 0/5 | 0/5 |
| 42.5 | 170.00 mg/4.0 ml 1.00 μl/gram | 0/5 | 0/5 |
| 81.25 | 170.00 mg/2.0 ml 1.00 μl/gram | ‡ | ‡ |
| 87.73 | 175.45 mg/2.0 ml | 2/4 | 2/4 |
| 102.47 | 102.47 mg/2.0 ml 2.00 μl/gram | 0/8 | ‡ |
| 133.0 | 99.75 mg/1.5 ml 2.00 μl/gram | ‡Note: Only one injection pure IV - the other two were all or mostly IM. | ‡ |
| 199.5 | 99.75 mg/1.0 ml 2.00 μl/gram | 1/1 | 1/1 |
| 199.5 | 99.75 mg/1.0 ml 3.00 μl/gram | 1/1 | 1/1 |

TABLE V $LD_{50}$(Oral) Studies

Compound: $CH_3(CH_2)_{10}CO_2CH_2-{}_+N$ (pyridinium) $Cl^-$, NCH$_3$

Animal: White Male Mice MCR-ICR Average Weight 21.9 grams. Fasted seven daytime hours prior to injection. Replaced in cage with food immediately after injection.

Procedure:

2 grams IRx-1229 weighed into weighing bottle. A 4 ml of 0.8% sodium chloride pH 7.0 added. Solution adjusted to pH 5.8 using saturated sodium bicarbonate. 0.01 ml injected per gram of mouse body weight to give 5 g/kg dose.

2 ml of above solution was diluted with 1 ml of 0.9% sodium chloride, pH 7.0 to give the second dose of 3.35 g/kg.

1 ml of the 3.35 g/kg dose was diluted 1:1 using 0.9% sodium chloride, pH 7.0 to give the third dose of 1.68 g/kg.

Results:

| Total Animals Used: | 30 |
|---|---|
| Total Doses: | 3 |
| Animals Per dose: | 10 |

24 hour $LD_{50}$: 4.3 g/kg
19/20 Confidence Limits: 1.76 g/kg (3.4–5.16 g/kg)
Slope: 1.35
19/20 Confidence Limits: 0.36 (1.18–1.54)
7 day $LD_{50}$: 4.11 g/kg
19/20 Confidence Limits: 3.2 g/kg (2.8–6.0 g/kg)
Slope: 1.84
19/20 Confidence Limits: 2.14 (1.06–3.2)

| DOSE (g/kg) | MORTALITY 24 HRS. | DEATHS PER DAY | | | | | | | MORTALITY 7 DAYS |
|---|---|---|---|---|---|---|---|---|---|
| | | Day 1 | Day 2 | Day 3 | Day 4 | Day 5 | Day 6 | Day 7 | |
| 5.00 | 7 | 7 | — | — | — | — | — | — | 7 |
| 3.35 | 2 | 2 | — | 1 | — | — | — | — | 3 |
| 1.68 | 0 | 0 | 1 | — | — | — | — | — | 1 |

Symptoms:
Severe diarrhea
Phonation
Inactivity
Rough Yellow Fur (survivors at 2 days)

Acute 7-Day Oral Toxicity: $LD_{50}$ 4.11 g/kg.

In comparison, the toxicity of cetylpyridinium chloride, a well-known "hard" quaternary surface active agent is set out below:

TABLE VI

TOXICITY OF CETYLPYRIDINIUM CHLORIDE

| Oral | - mouse | $LD_{50}$ | 108 mg/kg[1] |
|---|---|---|---|
| IP | - mouse | $LD_{50}$ | 10 mg/kg[2] |
| IV | - rat | $LD_{50}$ | 30 mg/kg[3] |

Toxic Substances List 1974 Edition

1. Proceedings of the Society for Experimental Biology and Medicine, 120, 511 (1965).

2. M. R. Warren, et al., *J. Pharmacol. Exptl. Therapeutics*, 74, 401 (1942).

3. J. W. Nelson and S. C. Lyster, *J. Amer. Pharm. Assoc., Sci. Ed.*, 35, 89 (1946).

As can be readily determined, the IP, IV and oral LD$_{50}$ for a selective compound of the present invention is some 14 to 16 times greater (on an intraperitoneal basis); some 3 to 4.5 times greater (on an intravenous basis) and some 40 times greater (on an oral basis) than that observed for cetylpyridinium chloride.

Similar LD$_{50}$ values will be obtained for the remaining compounds of the present invention when subjected to the abovedescribed LD$_{50}$ studies.

The compounds of formulas (I) and (II) find wide application as antibacterial agents in such preparations as mouthwashes, shampoos, soaps, cosmetic bases, etc. Such formulations can be prepared in accordance with any of the procedures disclosed in "REMIMGTON'S PHARMACEUTICAL SCIENCES" (Fourteenth Edition) 1970. Naturally, the antibacterial effective amount required for a compound of formula (I) or (II) will vary with the microorganism in question.

From the foregoing description, one of ordinary skill in the art can easily ascertain the essential characteristics of this invention, and without departing from the spirit and scope thereof, can make various changes and modifications of the invention to adapt it to various usages and conditions. As such, these changes and modifications are preferably, equitably and intended to be, within the full range of equivalence of the following claims.

What I claim is:

1. A quaternary ammonium compound of the formula:

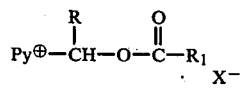

wherein Py is an N-heterocyclic unsaturated ring system comprising a basic nulceus selected from the group consisting of pyridyl and 3-carboloweralkoxypyridyl, 3-carbamoylpyridyl and 3-(N-loweralkylcarbamoyl)pyridyl; wherein R represents a member selected from the group consisting of hydrogen, $C_1$-$C_{20}$ alkyl, cycloalkyl having up to 7 carbon atoms, alkoxyalkyl having up to 20 carbon atoms, $C_1$-$C_{20}$ haloalkyl, carboxyalkyl having up to 20 carbon atoms, phenyl, naphthyl, substituted phenyl and substituted naphthyl whose substituents are selected from the group consisting of halogen, O—$C_1$-$C_4$ alkyl, O—$C_1$-$C_8$ acyl, wherein said acyl group is derived from a carboxylic acid, nitro, carboxyl, and carboethoxy; wherein R$_1$ represents C$_9$-C$_{22}$ straight or branched alkyl, —(CH$_2$)$_n$—

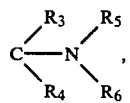

wherein R$_3$, R$_4$, R$_5$ and R$_6$ are each selected from the group consisting of hydrogen, methyl, and ethyl, C$_1$-C$_{22}$ straight or branched

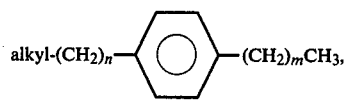

wherein n in each occurrence and m represent an integer of from 0 to 22, —(CH$_2$CH$_2$O)$_p$, wherein the p represents an integer of from 0 to 22, and the radical which results from decarboxylation of a naturally occuring bile acid; and wherein X is a nontoxic, pharmaceutically acceptable anion.

2. The compound as defined by claim 1, wherein Py is pyridyl.

3. The compound as defined by claim 1, wherein Py is 3-carboloweralkoxypyridyl, 3-carbamoylpyridyl and 3-(N-loweralkylcarbamoyl)pyridyl.

4. The compound as defined by claim 1, wherein Py is nicotinamide.

5. The compound as defined by claim 1, wherein Py is N-lower alkyl nicotinamide.

6. The compound as defined by claim 1, wherein Py is lower alkyl nicotinate.

7. The compound as defined by claim 1, wherein Py is pyridine.

8. The compound as defined by claim 1, wherein R is hydrogen.

9. The compound as defined by claim 2, wherein R is hydrogen.

10. The compound as defined by claim 3, wherein R is hydrogen.

11. The compound as defined by claim 4, wherein R is hydrogen.

12. The compound as defined by claim 5, wherein R is hydrogen.

13. The compound as defined by claim 6, wherein R is hydrogen.

14. The compound as defined by claim 7, wherein R is hydrogen.

15. The compound as defined by claim 1, wherein R is C$_1$-C$_{20}$ alkyl.

16. The compound as defined by claim 2, wherein R is C$_1$-C$_{20}$ alkyl.

17. The compound as defined by claim 3, wherein R is C$_1$-C$_{20}$ alkyl.

18. The compound as defined by claim 4, wherein R is C$_1$-C$_{20}$ alkyl.

19. The compound as defined by claim 5, wherein R is C$_1$-C$_{20}$ alkyl.

20. The compound as defined by claim 6, wherein R is C$_1$-C$_{20}$ alkyl.

21. The compound as defined by claim 7, wherein R is C$_1$-C$_{20}$ alkyl.

22. The compound as defined by claim 1, wherein R$_1$ is C$_9$-C$_{22}$ straight or branched alkyl.

23. The compound as defined by claim 2, wherein R$_1$ is C$_9$-C$_{22}$ straight or branched alkyl.

24. The compound as defined by claim 3, wherein R$_1$ is C$_9$-C$_{22}$ straight or branched alkyl.

25. The compound as defined by claim 4, wherein R$_1$ is C$_9$-C$_{22}$ straight or branched alkyl.

26. The compound as defined by claim 5, wherein R$_1$ is C$_9$-C$_{22}$ straight or branched alkyl.

27. The compound as defined by claim 6, wherein R$_1$ is C$_9$-C$_{22}$ straight or branched alkyl.

28. The compound as defined by claim 7, wherein R$_1$ is C$_9$-C$_{22}$ straight or branched alkyl.

29. The compound as defined in claim 1, wherein R is cycloalkyl having up to 7 carbon atoms.

30. The compound as defined by claim 1, wherein R is alkoxyalkyl having up to 20 carbon atoms.

31. The compound as defined by claim 1, wherein R is $C_1$-$C_{20}$ haloalkyl.

32. The compound as defined in claim 1, wherein R is carboxyalkyl having up to 20 carbon atoms.

33. The compound as defined by claim 1, wherein R is phenyl.

34. The compound as defined by claim 1, wherein R is naphthyl.

35. The compound as defined by claim 1, wherein R is the substituted phenyl.

36. The compound as defined by claim 1, wherein R is the substituted naphthyl.

37. The compound as defined by claim 1, wherein $R_1$ is

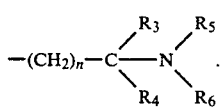

38. The compound as defined by claim 1, wherein $R_1$ is $C_1$-$C_{22}$ straight or branched alkyl

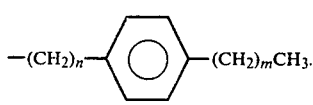

39. The compound as defined by claim 1, wherein $R_1$ is $-(CH_2CH_2O)_p$.

40. The compound as defined by claim 1, wherein X is selected from the group consisting of halide, methanesulfonate, fluorosulfonate and tosylate.

41. The compound as defined by claim 1, wherein X is selected from the group consisting of halide, methanesulfonate, fluorosulfonate and tosylate.

42. The compound as defined by claim 2, wherein X is selected from the group consisting of halide, methanesulfonate, fluorosulfonate and tosylate.

43. The compound as defined by claim 3, wherein X is selected from the group consisting of halide, methanesulfonate, fluorosulfonate and tosylate.

44. The compound as defined by claim 4, wherein X is selected from the group consisting of halide, methanesulfonate, fluorosulfonate and tosylate.

45. The compound as defined by claim 5, wherein X is selected from the group consisting of halide, methanesulfonate, fluorosulfonate and tosylate.

46. The compound as defined by claim 6, wherein X is selected from the group consisting of halide, methanesulfonate, fluorosulfonate and tosylate.

47. The compound as defined by claim 7, wherein X is selected from the group consisting of halide, methanesulfonate, fluorosulfonate and tosylate.

48. The compound of claim 1:
n-Octanoyloxymethylpyridinium chloride.

49. The compound of claim 1:
n-Dodecanoyloxymethylpyridinium chloride.

50. The compound of claim 1:
n-Tetradecanoyloxymethylpyridinium chloride.

51. The compound of claim 1:
n-Hexadecanoyloxymethylpyridinium chloride.

52. The compound of claim 1:
1-n-Dodecanoyloxymethyl-N-ethylnicotinamide chloride.

53. The compound of claim 1:
n-Octanoyloxymethyl-nicotinamide chloride.

54. The compound of claim 1:
n-Octanoyloxymethyl-nicotinamide bromide.

55. The compound of claim 1:
1-n-Octanoyloxymethyl-ethylnicotinate chloride.

56. The compound of claim 1:
1-n-Octanoyloxymethyl-ethylnicotinate bromide.

57. The compound of claim 1:
1-n-Octanoyloxymethyl-methylnicotinate chloride.

58. The compound of claim 1:
1-n-Octanoyloxymethyl-methylnicotinate bromide.

59. The compound of claim 1:
1-n-Decanoyloxymethyl-pyridinium chloride.

60. The compound of claim 1:
1-n-Decanoyloxymethyl-pyridinium bromide.

61. The compound of claim 1:
1-n-Decanoyloxymethyl-nicotinamide chloride.

62. The compound of claim 1:
1-n-Decanoyloxymethyl-nicotinamide bromide.

63. The compound of claim 1:
1-n-Decanoyloxymethyl-ethylnicotinate chloride.

64. The compound of claim 1:
1-n-Decanoyloxymethyl-ethylnicotinate bromide.

65. The compound of claim 1:
1-n-Tetradecanoyloxymethyl-nicotinamide chloride.

66. The compound of claim 1:
1-n-Tetradecanoyloxymethyl-nicotinamide bromide.

67. The compound of claim 1:
1-n-Tetradecanoyloxymethyl-ethylnicotinate chloride.

68. The compound of claim 1:
1-n-Tetradecanoyloxymethyl-ethylnicotinate bromide.

69. The compound of claim 1:
1-n-Tetradecanoyloxymethyl-methylnicotinate chloride.

70. The compound of claim 1:
1-n-Tetradecanoyloxymethyl-methylnicotinate bromide.

71. The compound of claim 1:
1-[α-(n-Octanoyloxy)ethyl]-pyridinium chloride.

72. The compound of claim 1:
1-[α-(n-Octanoyloxy)ethyl]-pyridinium bromide.

73. The compound of claim 1:
1-[α-(n-Octanoyloxy)ethyl]-nicotinamide chloride.

74. The compound of claim 1:
1-[α-(n-Octanoyloxy)ethyl]-nicotinamide bromide.

75. The compound of claim 1:
1-[α-(n-Octanoyloxy)ethyl]-N-ethylnicotinamide chloride.

76. The compound of claim 1:
1-[α-(n-Octanoyloxy)ethyl]-N-ethylnicotinamide bromide.

77. The compound of claim 1:
1-[α-(n-Octanoyloxy)ethyl]-ethylnicotinate chloride.

78. The compound of claim 1:
1-[α-(n-Octanoyloxy)ethyl]-ethylnicotinate bromide.

79. The compound of claim 1:
1-[α-(n-Decanoyloxy)ethyl]-pyridinium chloride.

80. The compound of claim 1:
1-[α-(n-Decanoyloxy)ethyl]-pyridinium bromide.

81. The compound of claim 1:
1-[α-(n-Decanoyloxy)ethyl]-nicotinamide chloride.

82. The compound of claim 1:
1-[α-(n-Decanoyloxy)ethyl]-nicotinamide bromide.

83. The compound of claim 1:
1-[α-(n-Decanoyloxy)ethyl]-N-ethylnicotinamide chloride.
84. The compound of claim 1:
1-[α-(n-Decanoyloxy)ethyl]-N-ethylnicotinamide bromide.
85. The compound of claim 1:
1-[α-(n-Decanoyloxy)ethyl]-ethylnicotinate chloride.
86. The compound of claim 1:
1-[α-(n-Decanoyloxy)ethyl]-ethylnicotinate bromide.
87. The compound of claim 1:
1-[α-(n-Dodecanoyloxy)ethyl]-pyridinium chloride.
88. The compound of claim 1:
1-[α-(n-Dodecanoyloxy)ethyl]-pyridinium bromide.
89. The compound of claim 1:
1-[α-(n-Dodecanoyloxy)ethyl]-nicotinamide chloride.
90. The compound of claim 1:
1-[α-(n-Dodecanoyloxy)ethyl]-nicotinamide bromide.
91. The compound of claim 1:
1-[α-(n-Dodecanoyloxy)ethyl]-N-ethylnicotinamide chloride.
92. The compound of claim 1:
1-[α-(n-Dodecanoyloxy)ethyl]-N-ethylnicotinamide bromide.
93. The compound of claim 1:
1-[α-(n-Hexadecanoyloxy)ethyl]-pyridinium chloride.
94. The compound of claim 1:
1-[α-(n-Hexadecanoyloxy)ethyl]-pyridinium bromide.
95. The compound of claim 1:
1-[α-(n-Hexadecanoyloxy)ethyl]-nicotinamide chloride.
96. The compound of claim 1:
1-[α-(n-Hexadecanoyloxy)ethyl]-nicotinamide bromide.
97. The compound of claim 1:
1-[α-(n-Hexadecanoyloxy)ethyl]-N-ethylnicotinamide chloride.
98. The compound of claim 1:
1-[α-(n-Hexadecanoyloxy)ethyl]-N-ethylnicotinamide bromide.
99. The compound of claim 1:
1-[α-(n-Hexadecanoyloxy)ethyl]-ethylnicotinate chloride.
100. The compound of claim 1:
1-[α-(n-Hexadecanoyloxy)ethyl]-ethylnicotinate bromide.
101. The compound of claim 1:
1-Oleyloxymethyl-pyridinium chloride.
102. The compound of claim 1:
1-Oleyloxymethyl-pyridinium bromide.
103. The compound of claim 1:
1-Oleyloxymethyl-nicotinamide chloride.
104. The compound of claim 1:
1-Oleyloxymethyl-nicotinamide bromide.
105. The compound of claim 1:
1-Oleyloxymethyl-N-ethylnicotinamide chloride.
106. The compound of claim 1:
1-Oleyloxymethyl-N-ethylnicotinamide bromide.
107. The compound of claim 1:
1-Oleyloxymethyl-ethylnicotinate chloride.
108. The compound of claim 1:
1-Oleyloxymethyl-ethylnicotinate bromide.

* * * * *